United States Patent [19]

Cone, Jr.

[11] Patent Number: 4,724,230
[45] Date of Patent: Feb. 9, 1988

[54] METHOD FOR PRODUCING ONCOLYSIS

[75] Inventor: Clarence D. Cone, Jr., Yorktown, Va.

[73] Assignee: Therapeutical Systems Corp., Yorktown, Va.

[21] Appl. No.: 634,267

[22] Filed: Jul. 25, 1984

Related U.S. Application Data

[63] Continuation-in-part of Ser. No. 419,324, Sep. 17, 1982, abandoned.

[51] Int. Cl.$^4$ .................. A61K 31/20; A61K 31/195; A61K 31/045
[52] U.S. Cl. .................................. 514/558; 514/561; 514/728
[58] Field of Search ................ 424/348; 514/728, 449, 514/561, 558

[56] References Cited

U.S. PATENT DOCUMENTS 4,196,300 4/1980 Mohrbacher et al. ................ 549/90

OTHER PUBLICATIONS

Weber, G., "Biochemical Strategy of Cancer Cells and the Design of Chemotherapy: G.H.A. Clowes Memorial Lecture", Cancer Research 43: 3466–3492 (Aug. 1983).

Wesdorp, R.I.C. et al., "Cancer Cachexia and its Nutritional Implications" Br. J. Sur. 70(6): 352–355 (Jun. 1983).

King, M. M., et al., "Modulation of Tumor Incidence and Possible Mechanisms of Inhibition of Mammary Carcinogensis by Dietary Antioxidents", Cancer Research (Suppl.) 43: 2485s–2490s (May 1983).

Rogers, A. E., "Influence of Dietary Content of Lipids and Liptropic Nutrients on Chemical Carcinogensis in Rats", Cancer Research (Suppl.) 43: 2477s–2484s (May 1983).

Weinhouse, S., "Changing Perceptions of Carbohydrate Metabolism in Tumors". Molecular Interrelations of Nutrition and Cancer, edited by M. S. Arnott, et al., Raven Press, New York (1982) pp. 167–181.

Weber, G., "Differential Carboxydrate Metabolism in Tumor and Host", Molecular Interrelations of Nutrition and Cancer, edited by M. S. Arnott, Raven Press, New York (1982) pp. 191–208.

Kritchevsky, D., "Lipids and Cancer", Molecular Interrelations of Nutrition and Cancer, edited by M. S. Arnott, et al., Raven Press, New York, (1982) pp. 209–217.

Kidwell, W. R., et al., "Effect of Unsaturated Fatty Acids on the Development and Proliferation of Normal and Neoplastic Breast Epithelium", Molecular Interrelations of Nutrition and Cancer, edited by M. S. Arnott, et al., Raven Press, New York (1982) pp. 219–236.

Carroll, K. K., et al., "The Rolle of Lipids in Tumorigensis", Molecular Interrelations of Nutrition and Cancer, edited by M. S. Arnott, et al., Raven Press, New York (1982) pp. 237–245.

Lavietes, B. B., et al., "The Role of Lipid Metabolism in Neoplastic Differentiation", J. Theor. Biol. 85: 523–542 (1980).

Wicha, M. S., et al., "Effects of Free Fatty Acids on the Growth of Normal and Neoplastic Rat Mammary Epithelial Cells", Cancer Research 39: 426–435 (Feb. 1979).

Burns, C. P., et al., "Utilization of Long-Chain Free Fatty Acids and Glucose by Human Leukemic Blast Cells" Cancer Research 37: 1323–1327 (May 1977).

(List continued on next page.)

Primary Examiner—J. R. Brown
Assistant Examiner—John W. Rollins

[57] ABSTRACT

An improved method is described for producing oncolysis, including regression of malignant tumors or other malignant conditions, without adverse effects upon normal body cells. In addition to a calorically and compositionally defined nutritional regimen providing a minimum of amino acids and fatty acids and a maximum of carbohydrate, administered concurrently with a drug regimen of an agent or agents that uncouple oxidative phosphorylation (most preferably 2,4-dinitrophenol), there is also concurrently administered a selected amount of a substantially non-toxic fatty acid oxidation inhibitor capable of effectively lowering the mitochondrial $\beta$-oxidation rate of fatty acids.

21 Claims, 1 Drawing Figure

OTHER PUBLICATIONS

Littman, M. L., et al., "Effect of Cholesterol-Free, Fat-Free Diet and Hypocholesteremic Agents on Growth of Transplantable Animal Tumors", Cancer Chemotherapy Reports 50(1 and 2); 25–45 (1966).

Lehninger, A. "Oxidation of Fatty Acids in Animal Tissues" Chapter 18, (1982).

Olowe, U., et al., The Journal of Biological Chemistry 257(10): 5408–5413 (1982).

Raaka, B. M. et al., The Journal of Biological Chemistry 254(9): 3303–3310 (1979).

Raaka, B. M., et al., The Journal of Biological Chemistry 254(14): 6755–6762 (1979).

Fong, J. C., et al., "On the Rate-Determining Step of Fatty Acid Oxidation in Heart Inhibition of Fatty Acid Oxidation by 4-Pentenoic Acid", The Journal of Biological Chemistry, 253(19): 6917–6922 (1978).

Feldman, E. B., et al., "Circulating Lipids and Lipoproteins in Women with Metastaic Breast Carcinoma", J. Clin. Encrinol. & Metab. 33:8 (1971).

Weinhouse, S., "Metabolism and Isozyme Alterations in Experimental Hepatomas", Federation Proceedings 32(12): 2162–2167 (1973).

Kitada, S., et al., "Characterization of a Lipid Mobilizing Factor from Tumors", Golden Jubilee International Congress on Essential Fatty Acid and Prostaglandins, edited by R. T. Holman et al., Pergamon Press, New York, (1981).

Bloch-Frankethal, L., et al., "Fatty Acid Oxidation and Ketogensis in Transplantable Liver Tumors", Cancer Research 25(5): 732–36 (1965).

Merck Index, Tenth Ed., Merck & Co., Inc. Rahway, NJ (1983) (specific paragraph citations in main text, pp. 26–27).

Heatler P. G. Inhibition of Mitochondrial Functions, Pergamon, 1981.

Chemical Abstr. 73:12786f, 1970; 73:18358h, 1970; 69:65737q, 1968; and 70; 1785s, 1969.

Busch, H. An Introduction to Biochem. of Cancer Cell Ch. 10, Acad. Press, N.Y., 1962.

Demers, L. M. et al., Proc. Soc. Exper. Biol. M. 140:724, 1972.

Hemker, H. C. BBA 48:221, 1961.

Haskell Cancer Treatment, Saunder Co. Pa., 2nd ed. 1985, Chg. to 76, pp. 889–896.

Burns C. P., et al., "Fatty Acid Utilization by L1210 Murine Leukemia Cells" Cancer Research 37: 1991–1997 (Jul. 1977).

Cederbaum; I. A., et al., "Fatty Acid Oxidation, Substrate Shuttles, and Activity of the Citric Acid Cycle in Hepatocellular Carcinomas of Varying Differentiation", Cancer Research 36: 2980–2987 (Sep. 1976).

Spector, A. A., et al., "Fatty Acid Metabolism in Tumors", Progr. biochem. Pharmacol., 10: 42–75 (Krager, Basel 1975).

Sabine, J. R., "Defective Control of Lipid Biosynthesis in Cancerous and Precancerous Liver" Progr. biochem. Pharmacol., 10: 269–307 (Krager, Basel 1975).

Carroll, K. K., "Dietary Fat in Relation to Tumorigensis", Progr. biochem. Pharmacol., 10: 308–353 (Krager, Basel 1975).

van Eys, J., "Nutrition and Neoplasia", Nutrition Reviews 40(12); 353–359 (1982).

Buzby, G. P., et al., "Host-Tumor Interaction and Nutrient Supply", Cancer 45(12): 2940–2948 (1980).

METHOD FOR PRODUCING ONCOLYSIS

This application is a continuation-in-part of U.S. Ser. No. 06/419,324, filed on Sept. 17, 1982, now abandoned. Reference is made to Disclosure Document No. 126,961, filed by the present inventor on Apr. 26, 1984. Permanent retention thereof is hereby requested.

FIELD OF THE INVENTION

The Cone Uncoupling Agent Cancer Therapy System (CUACT, CUACTS or CUACT SYSTEM), a unique drug-supplemented nutritional therapeutical regimen which produces efficacious regression of malignant neoplasms of a wide variety, and without toxic side-effects, is described in detail in U.S. Ser. No. 06/419,324, filed on Sept. 17, 1982. The present invention comprises means whereby the basic rate and extent of oncolysis normally effected by the CUACTS per se can be substantially increased.

BACKGROUND OF THE INVENTION

As explained more fully in the parent application, the CUACT SYSTEM acts to effect lysis and regression of malignant tumors and neoplasms in vivo by depressing the rate of production of adenosine triphosphate (ATP) selectively in cancer cells to a level below that required to maintain cellular viability. Said lethal lowering of the ATP production rate selectively in cancer cells is based upon the general phenomenon that cancer cells are unable to fully utilize glucose, the primary ATP source of normal cells, to generate significant amounts of ATP. Because of their malignant-transformation induced inability to significantly utilize glucose for ATP energy production, cancer cells are almost entirely dependent upon the oxidation of amino acids and fatty acids for production of ATP at rates required for maintenance of viability and proliferation. This metabolic aberrancy of cancer cells is exploited by CUACTS, wherein a Defined Nutritional Regimen (Dnr) is used to minimize dietary amino acid and fatty acid availability to the cancer cells while providing a level of glucose which is adequate for the ATP energy generation needs of normal (nonmalignant) body cells. The Dnr thereby selectively and substantially lowers the maximum available rate at which the cancer cells can produce ATP. Simultaneously, one or more uncoupling agents is administered to effectively uncouple oxidative phosphorylation (O-P uncoupling) in the cell mitochondria, thereby further substantially reducing the maximum rate at which ATP can be produced in the cancer cells. The uncoupling agent, when administered according to a prescribed patient-specific dosage schedule, as more fully described in the parent application, to produce adequate rates of uncoupling, ultimately effects a lethal reduction of the ATP generation rate in the cancer cells selectively. Since the normal cells readily utilize the calorically adequate glucose provided by the dietary carbohydrate source in the Dnr, they experience no net lowering of their ATP-production rate and thus maintain a fully normal rate of ATP production despite the uncoupling action.

It has now been discovered that the oncolytic efficacy of the above-mentioned CUACTS regimen may be lessened in certain cases by high availability of fatty acids mobilized from endogenous sources. The present invention comprises the concomitant clinical in vivo administration, with the CUACTS regimen, of an agent or agents (FAOI) which inhibit fatty acid oxidation in the mitochondria of cancer cells, thereby effecting a direct control over the availability of plasma fatty acids for use in ATP energy production by the cancer cells, regardless of the exogenous (dietary) or endogenous source of the plasma fatty acids.

BRIEF DESCRIPTION OF THE INVENTION

The present invention affords a novel method of substantially reducing or eliminating a wide variety of malignancies in humans or other mammals. Specifically, the invention comprises the administration, either concomitantly with the CUACTS regimen as described in the parent application, or independently, of an agent or agents (FAOI) which effectively inhibit $\beta$-oxidation of fatty acids in cellular mitochondria in vivo. This novel therapeutic method thereby enhances the rate of oncolysis—that is, lysis, degeneration or death of malignant cells—by insuring an adequate inhibition of fatty acid availability for ATP energy production in malignant cells. The method in combination with CUACTS is termed CUACTS+FAOI, or CUACTS F.

The present invention contemplates that the Defined Nutritional Regimen (Dnr) which is one of the two therapeutic regimens comprised by the CUACT SYSTEM may be modified to avoid the development of untoward or deleterious hypoglycemia when the FAOI is administered in conjunction with CUACTS.

Symbols and Definitions

As used herein:

$B_S$=standard basal metabolic rate (Kcal/day): determined from the Mayo Normal Standard Basal Metabolic Rate Tables from patient's sex, age, height, and weight at the beginning of treatment [see American Journal of Physiology, July, 1936]; the directly measured standard (i.e., without uncoupling agent) basal metabolic rate in the case of nonprimate mammalian subjects.

$B_T$=therapeutic basal metabolic rate (Kcal/day): the basal (resting) metabolic rate determined in the standard clinical manner with indirect calorimetry procedures ($O_2$ consumption rate measurement with conversion to equivalent Kcal/day), but with the subject receiving the CUACTS uncoupling agent.

$B_T'$=normalized therapeutic basal metabolic rate (non-dimensional): a nondimensional representation of the $B_T$ obtained by dividing $B_T$ by $B_S$; thus $B_T'$ is the number of multiples of $B_S$ contained in $B_T$; used to specify target $B_T$ of subject to be achieved by appropriate dosage schedule of uncoupling agent.

$A_T$=therapeutic active metabolic rate (Kcal/day): the measured metabolic rate of the subject ($O_2$ consumption rate measurement with conversion to equivalent Kcal/day) under activity conditions representative of the particular individual's average daytime active state (e.g., measurement made with subject sitting or standing, soon after eating).

$\frac{1}{2}(B_T+A_T)$=overall therapeutic metabolic rate (Kcal/day): the total daily (24 hour) caloric expenditure of the subject as determined using the measured $B_T$ (Kcal/day) and $A_T$ (Kcal/day) of the subject; used to determine the total daily caloric intake required for maintenance of overall caloric balance.

Kcal=kilocalorie (1000 gram-calories)

Note: The pretreatment basal metabolic rate and pretreatment active metabolic rate of the patient are measured in exactly the same manner as are the subsequent $B_T$ and $A_T$ maintaining during the treatment period per se. The pretreatment overall metabolic rate is determined as one-half of the sum of the pretreatment basal metabolic rate and the pretreatment active metabolic rate.

Other definitions also appear in other portions of this application.

DETAILED DESCRIPTION OF THE INVENTION

Figure 1:
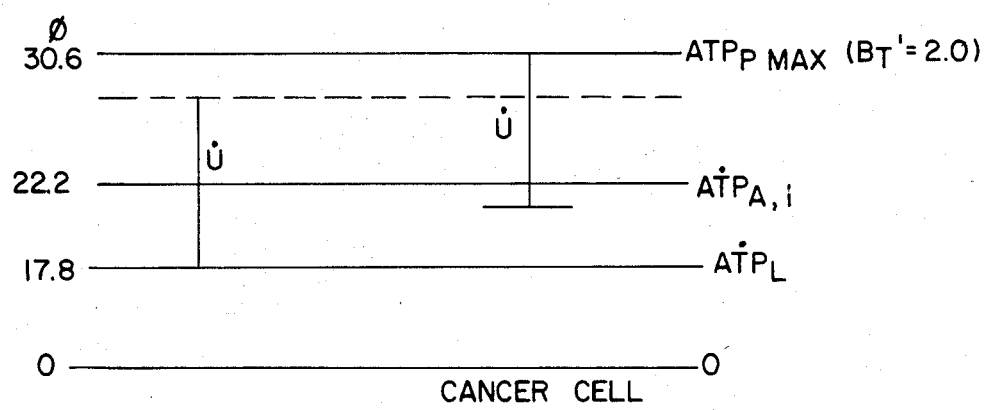

It is emphasized that the therapeutic regimen of this invention, like the CUACT regimen as defined and described in the parent application, must be individually prescribed and monitored by trained professionals.

The oncolytic efficacy of the CUACTS treatment regimen may be adversely affected in certain cases by the availability of fatty acids mobilized from endogenous sources. As the parent application teaches, the key requirement for realizing the full oncolytic efficacy of the CUACT SYSTEM is to effectively restrict the availability of fatty acids and amino acids to the cancer cells. Dietary sources of amino acids and fatty acids are effectively minimized by prescription and administration of a patient-specific Defined Nutritional Regimen of the CUACTS. However, amino acids and fatty acids supplied to the blood plasma by mobilization from endogenous protein and fat deposits of the body are often not directly controllable by dietary manipulation. The plasma levels of endogenously derived fatty acids, during clinical administration of the CUACTS, may be of sufficient magnitude, particularly in obese patients, to reduce significantly the overall rate and extent of oncolysis which otherwise would be achievable with the CUACTS.

Detailed clinical testing and experience with the administration of CUACTS have shown that endogenously derived amino acids are only minimally available for oxidation by the cancer cells in nearly all cancer patients undergoing treatment with the CUACT SYSTEM. Fatty acids from endogenous sources, however, are frequently found to be present in substantial concentration in the plasma of cancer patients undergoing treatment with the CUACTS, especially obese patients. For the purpose of this application, a substantial concentration of fatty acids is defined as that concentration which will inhibit and impair the oncolytic effectiveness of the CUACTS in a given individual by providing a steady source of oxidative energy to the cancer cells, sufficient to prevent reduction of their net ATP production rate to the lethal level by the uncoupling agent. It is possible with the CUACTS to overcome the effect of the fatty acid availability rate permitted by a normal fatty acid concentration level (i.e., approximately 8-30 mg unesterified fatty acid per 100 deciliters of plasma) in the cancer patient by imposition of adequate O-P uncoupling concomitantly with the Dnr. However, the fatty acid concentration in the plasma of advanced cancer patients is frequently found to be sufficiently above this normal level to prevent the achievement of very significant oncolysis with the CUACTS regimen per se. Generally, it is not possible to overcome such elevated fatty acid concentrations simply by increasing the uncoupling rate with increased dosage of the uncoupling agent of the CUACTS, since at metabolic rates above that which can be calorically satisfied by the maximal exogenous caloric intake of the Dnr, the caloric deficiency induces a significant and sustained mobilization of fatty acids from endogenous body adipose and omental fat depots. The increase in fatty acid availability rate thus produced more than compensates for the concomitant increased O-P uncoupling. Thus, it is not possible clinically to increase the uncoupling rate enough to overcome the greatly increased fatty acid availability from the mobilized endogenous sources above the point of dietary satiation, or thereby to effect the desired maximal rate and extent of oncolysis with the CUACTS per se.

The present invention comprises, in one respect, the clinical administration in vivo, concomitant with the CUACTS dietary regimen as described in the parent application, or a modified version thereof, and the CUACTS uncoupling agent, as likewise therein described, of an agent or agents (FAOI) effective to inhibit fatty acid oxidation in the mitochondria of cancer cells. This, in turn, effects a direct control over the availability of plasma fatty acids in the cancer cells for use in ATP energy production, regardless of the exogenous or endogenous source of the plasma fatty acids. By use of FAOI at adequate dosage, fatty acid availability in the cancer cells for ATP production can be readily reduced to levels which permit the O-P uncoupling produced by the uncoupling agent to effect maximally rapid oncolysis rates and extents, despite the presence of a substantially elevated fatty acid concentration in a particular cancer patient's plasma. Of course, those normal cells of the body which oxidize fatty acids also experience the fatty acid oxidation inhibition produced by the FAOI, but since the normal cells can fully utilize the abundant glucose provided by the Defined Nutritional Regimen of the CUACTS, they experience no net reduction in the ATP prooduction rate below the normal level, and thus experience no untoward or adverse effects. Consequently, with concurrent use of clinically tolerable uncoupling and fatty acid oxidation inhibition rates, rapid oncolysis is routinely achieved, irrespective of the plasma fatty acid concentration, and the treatment can be monitored and continued until complete oncolysis is effected (i.e., a true clinical cure is achieved), all without overt toxicity or adverse side-effects.

A most advantageous feature of the embodiment of the present invention that comprises the use of FAOI with the CUACTS regimen is that, because of the high degree of fatty acid oxidation inhibition achievable with various FAOI, the level of uncoupling (and hence elevation in patient overall therapeutic metabolic rate) necessary to effect very significant oncolysis rates can be substantially reduced. This enables fully efficacious treatment of a broad range of cancer patients whose advanced age, enfeebled condition, and/or far-advanced disease state (whether due to cancer or other pathological states) would have prevented or impaired their ability to withstand treatment at significantly elevated overall therapeutic metabolic rates.

Fatty acid oxidation inhibitory agents are available which are capable of effecting as high as 100% inhibition of fatty acid oxidation in cellular mitochondria. By routinely utilizing FAOI concomitantly with the CUACTS, one avoids those adverse clinical situations wherein the endogenous fatty acid availability of the particular cancer patient under treatment is in substantial concentration and hence inhibits the efficacy of the CUACTS regimen alone. For example, one such situation so avoided occurs when the fatty acid concentration of a particular individual's plasma idiosyncratically elevates to deleteriously high levels during the course of treatment with CUACTS alone due to mobilization at the elevated therapeutic metabolic rate of fatty acids from fat depots. Moreover, in the case of patients with very large tumor burdens, wherein overly rapid lysis of tumor cells could result in toxemia from tumor products, modulation of the rate of oncolysis is achievable through appropriate variation of the FAOI administration schedule.

Substantial oncolysis may be achieved with adequately high levels of inhibition of fatty acid oxidation rates by use of FAOI alone at adequately high dosage levels. (See Example 8 hereinafter.) Since, in this special case of the present invention, the therapeutic basal metabolic rate with FAOI alone does not increase above the pretreatment basal metabolic rate, there is no elevation of the oxygen consumption rate of the patient—a condition which may be of great advantage in the treatment of particular cancer patients, especially those having compromised pulmonary capacity because of their malignancy (e.g., lung tumors) or other attendant complications (e.g., emphysema, cardiac insufficiency). Similarly, the total daily caloric intake required for overall daily caloric balance remains equal to that of the pretreatment overall therapeutic metabolic rate, so that no problems pertaining to Dnr intake satiation are encountered—a condition of particular advantage in cancer patients whose digestion and/or absorptive capacities may be appreciably compromised by their malignant disease or complicating factors. In general, however, the relatively large percentage inhibition of the fatty acid oxidation rate required to effect significant oncolysis by use of FAOI alone (e.g., see Example 8) could potentially lead to toxic side-effects in such normal cells as naturally utilize fatty acids as a significant energy source (e.g., muscle, kidney) if maintained for an extended period of time. If the maximum FAOI dosage level has to be restricted appreciably for the foregoing reason, there may be inadequate fatty acid oxidation rate inhibition to effect significant oncolysis, particularly in cases wherein the increase in amino acid oxidation rate and increased glycolysis rate in the cancer cells, in homeostatic response to the imposed fatty oxidation rate decline, is substantial. Consequently, the utilization of the basic CUACTS treatment regimen with the concomitant administration of adjuvant FAOI at optimum dosage schedule to produce a maximum oncolysis rate without adverse side-effects or toxicity is the preferred overall treatment regimen according to the present invention. This preferred embodiment is further favored by the ability conferred thereby to accommodate special cancer patient cases by suitably adjusting either the uncoupling aspect or the FAOI aspect, or both, to clinically optimize the treatment for variously physiologically compromised patients.

For the purposes of the present invention, any agent or agents or procedure which results in an inhibition of the mitochondrial $\beta$-oxidation rate of fatty acids (of any class or chain length) in concurrent administration with the CUACTS regimen as more fully described in the parent application constitutes a fatty acid oxidation inhibitor or fatty acid oxidation inhibition agent (FAOI) within the scope of this invention. Fatty acid oxidation inhibition may be effected by the FAOI by retarding mobilization of fatty acids from endogenous sources (e.g., by administration of insulin), or by retarding the rate of transport of fatty acids into mitochondria through interfering at any point of the carnitine-fatty acid shuttle cycle, or through inhibiting the biochemical oxidation per se of fatty acids by blocking any enzyme-mediated transformation step therein, or by any combination of the foregoing.

For medical application in cancer therapy, such FAOI must also, of course, be clinically tolerable, i.e., free of overt toxicity and/or unacceptable side-effects.

Among the FAOI agents which can be used in practicing the present invention are: orotic acid, dichloroacetic acid, 4-pentenoic acid, $\alpha$-amanitin, valproic acid, bromstearic acid, 2-bromooctanoic acid, hydrazine monohydrate, 1-phenyl-3-pyrazolidone, phenylpyruvic acid, $\alpha$-ketoisocaproic acid, methylenecyclopropylacetic acid, biguanides, 2-tetradecylglycidic acid, methyl 2-tetradecylglycidate, malonyl CoA, D-acetylcarnitine, D-carnitine, deoxycarnitine, deoxynorcarnitine, L-carnitine, D-palmitoyl-carnitine, D-decanoylcarnitine, crotonyl CoA, $\Delta$2,3-hexadecenoyl CoA, p-chloromercuribenzoic acid, and N-ethyl-maleimide. The foregoing is intended to be a representative but not exhaustive listing of FAOI agents which can be used in practicing the present invention. Any one or any combination of such agents may be employed as the FAOI of the present invention, commensurate with the tolerability of their in vivo use.

Of the aforementioned FAOI agents, 2-tetradecylglycidic acid and methyl 2-tetradecylglycidate have received evaluation in vivo (for potential reduction of diabetic hyperglycemia; U.S. Pat. No. 4,196,300) and have been shown to be highly effective in producing fatty acid oxidation inhibition without attendant acute side effects. Consequently, 2-tetradecylglycidic acid and methyl 2-tetradecylglycidate are considered the preferred FAOI for use in the present invention.

The FAOI may be administered orally (preferentially) or parenterally.

When practicing the present invention, a modification of the specific embodiment of the Defined Nutritional Regimen (Dnr) schedule disclosed at pages 23-27 of U.S. Ser. No. 06/419,324 may advantageously be utilized in many instances. Thus, in lieu of six nutritional cocktails each containing one-sixth of the full 24-hour caloric requirement and given at 2-hour intervals from 8 AM through 6 PM, the Dnr schedule now preferred for use with FAOI involves three important features: First, the 24-hour caloric allowance is divided into eight nutritional cocktails, administered at 2-hour intervals from 6 AM through 4 PM, and also at 8 PM and at 12 PM. Second, these drinks are no longer of equal caloric content. The first two drinks in the morning (at 6 AM and 8 AM) each have their basic caloric content—as calculated by dividing the 24-hour caloric requirement by eight—increased by $\frac{1}{4}$ of the patient-specific glycogen Kcal storage capacity of the liver and extracellular fluid. For example, the glycogen storage capacity of the liver and extracellular fluid of an individual of 70 Kg body weight is 360 Kcal and that for other body weights is determined by multiplying 360 Kcal by the quotient $$\frac{\text{Body Weight (Kg)}}{70 \text{ (Kg)}}$$

(See White, A., et al., *Principles of Biochemistry*, 5th Ed., p. 478, McGraw-Hill Co., N.Y., N.Y.) Conversely, the two nighttime drinks (at 8 PM and 12 PM) each have the aforementioned basic caloric content decreased by $\frac{1}{2}$ of the calculated glycogen storage capacity of the liver and extracellular fluid. Third, the essential fatty acid component of the Dnr disclosed in the parent application is eliminated.

This Dnr schedule essentially furnishes calories at the same rate as they are required for immediate metabolic support by both spreading the caloric intake more evenly throughout the 24-hour period and by varying the caloric content of the drinks to reflect the diurnal energy requirements of the patient. The additional caloric content of the 6 AM and 8 AM drinks replenishes the glycogen store, while the decreased caloric content of the 8 PM and 12 PM drinks allows the stored glycogen to be mobilized, thus maintaining the normal pattern of glycogen metabolism. Under the CUACTS regimen, about 30 to 40% of the daytime glucose intake is converted to fatty acids, which are subsequently mobilized from adipose storage to support metabolic needs during the nighttime. The intent of the hereindescribed modified Dnr schedule is to substantially and advantageously preclude dietary glucose from being converted into fatty acids which could be metabolized by the cancer cells if FAOI were not present, but would be unavailable to normal cells during the nighttime in the presence of the FAOI, thus leading to development of a hypoglycemic state. Moreover, the maximum degree of uncoupling permissible is determined by the maximum dietary (plus any supplemental parenteral) caloric intake required in order to maintain caloric balance and thus preclude mobilization of adipose fatty acids. And, since satiation in turn determines the maximum dietary intake, the substantial increase in dietary caloric intake before satiation occurs obtainable with this Dnr schedule permits the maximum degree of permissible uncoupling to be increased commensurately, with a substantial increase in efficacious oncolytic rate and extent.

The modified Dnr schedule embodiment just described is most advantageously employed when a fatty acid oxidation inhibitor is administered concurrently with the CUACT SYSTEM. Otherwise, due to the inhibitory effect of the FAOI the aforementioned 30 to 40% of the 24-hour caloric requirement which would be shunted into adipose storage under the 6-cocktail, daytime Dnr would not be generally available for body use. Because this fatty acid-stored caloric supply could not be used, a major toxic state of energy depression, with symptoms of acute hypoglycemia, could develop. However, by providing dietary calories (principally as glucose) at 8 PM and at 12 PM the aforementioned conversion to fatty acids is largely precluded, and the risk of hypoglycemia development during administration of CUACTS+FAOI is consequently eliminated.

In order to maximize the restriction of dietary fat intake in the modified Dnr regimen, the essential fatty acid component of the CUACTS regimen is preferably omitted in its entirety during the period of administration of the FAOI. Since body fatty acid turnover (oxidation), including that of essential fatty acids, is substantially reduced with the FAOI and since the period of administration of the FAOI is relatively short, as hereinbelow described, this omission of essential fatty acids from the modified Dnr regimen has no adverse nutritional consequences.

The Dnr regimen embodiment described herein may also be employed advantageously in the CUACT SYSTEM alone. Since it precludes the conversion of some 30% to 40% of the dietary glucose of fatty acid which, upon mobilization at night, would become available to the cancer cells, this Dnr schedule per se may considerably enhance the oncolytic effectiveness of the CUACT SYSTEM in some patients. This Dnr schedule also has the general advantage of decreasing the liquid volume of the daytime cocktails, thereby forestalling satiation and facilitating patient compliance in orally ingesting the required amount of calories.

The aforementioned patient-specific 24-hour caloric requirement can be administered by a combination of orally ingested Dnr components plus supplemental parenterally supplied glucose. It is possible to increase the maximum overall glucose intake rate above that possible with the oral Dnr intake alone by supplemental intravenous feeding of glucose, thereby allowing some increase in the maximum uncoupling rate without exogenous caloric deficiency. Dnr glucose plus supplemental parenterally supplied glucose is used herein to define the satiation limit of the maximum metabolic rate in CUACTS+FAOI. Parenteral feeding of glucose, supplemental to or as the Dnr, can be very significant for patients whose alimentary absorption has been impaired by tumor growth, surgery and/or mitotoxin chemotherapy. Moreover, the maximum use of supplemental parenteral glucose feeding will be critical in treating any patient who has idiosyncratically entered the state of severe hypoglycemia, due to whatever cause, while on the CUACTS+FAOI regimen.

EXAMPLE 1

As a representative embodiment of the present invention, the following example is illustrative. The cancer patient is administered the CUACTS treatment regimen, as described in U.S. Ser. No. 06/419,324, comprising a defined nutritional regimen—here in the form of the above-described eight-cocktail Dnr without essential fatty acids—and an adequate dosage schedule of uncoupling agent, e.g., 2,4-dinitrophenol, to reach and maintain a maximum tolerable therapeutic basal metabolic rate ($B_T$) equal to 1.5 to 2.5 times the standard (Mayo) basal metabolic rate $B_S$ (American Journal of Physiology, July, 1936) of the patient, said maximum tolerable therapeutic basal metabolic rate, $B_T$ (i.e., due to the associated elevated uncoupling rate) within this range being determined as that therapeutic basal metabolic rate $B_T$ at which the onset of satiation precludes further Dnr intake to effect overall caloric balance (i.e., total daily caloric intake equals total daily caloric expenditure where the latter is given by $\frac{1}{2}(B_T+A_T)$Kcal/day) with or without supplemental parenteral administration of glucose. Then the FAOI is administered in adequate dosage schedule to achieve a percentage inhibition of fatty acid oxidation sufficient, in combination with the stated maximum tolerable uncoupling rate, to effect a significant or satisfactory rate of oncolysis. The percentage inhibition of the fatty acid oxidation rate for optimal oncolysis under these conditions may range from 20% to 60%, depending upon the individual patient, the particular tumor type and stage, and the initial fatty acid concentration of the plasma. The percentage by which fatty acid oxidation is depressed by the FAOI is simply monitored in vivo by measuring the overall respiratory quotient (RQ, defined as liters of $CO_2$ produced per liter of $O_2$ consumed), at the same time that the daily metabolic rate measurements ($B_T$, $A_T$) are made, and calculating therefrom the percentage reduction in $CO_2$ production rate (or equivalent Kcal/day) from fatty acid oxidation per se effected by the FAOI. In general, the higher the percentage of fatty acid oxidation rate inhibition that can be achieved, the greater will be the rate of oncolysis, (i.e., percentage decrease in tumor mass per unit time), but patient response variability and tolerance will be the ultimate guiding criterion.

The concomitant administration of the defined nutritional regimen, uncoupling agent, and FAOI is continued for 7 to 14 days, or until the incipient onset of fatigue or other symptoms. After intervening rest periods of approximately 5 to 7 days the treatment regimen is repeated until clinically complete tumor lysis is achieved.

EXAMPLE 2

Alternatively, the FAOI may be administered before the uncoupling agent. The FAOI is administered at progressively increasing dosage level so as to achieve the maximum clinically tolerable percentage of fatty acid oxidation inhibition for the individual patient, generally in the range of approximately 20% to approximately 60% and preferably 50%, concomitantly with the modified Dnr regimen, said percentage fatty acid oxidation rate inhibition being assayed by RQ measurement as heretofore described. For example, the patient will receive a graded dosage of FAOI adequate to effect a target 50% inhibition of fatty acid oxidation—relative to the rate of fatty acid oxidation measured via the respiratory quotient while on the Dnr (without essential fatty acids) prior to administration of the FAOI. If any untoward problems are encountered, the FAOI dosage will not be further increased; that percentage of inhibition, or a lesser and more tolerable percentage will be used as the maximum for that patient.

Then, while maintaining the maximum tolerable percentage fatty acid oxidation rate inhibition, the uncoupling agent is administered at graded dosage so as to attain the maximum tolerable overall therapeutic metabolic rate, i.e., $\frac{1}{2}(B_T+A_T)$Kcal/day, as determined by the onset of dietary Dnr intake satiation (with or without supplemental parenterel administration of glucose) for the individual patient, beyond which caloric balance cannot be maintained. The patient is monitored for any evidence of problems, especially hypoglycemia. The concomitant and steady-state administration of the defined nutritional regimen, the FAOI and the uncoupling agent is continued for 7 to 14 days, or until the incipient onset of fatigue or other symptoms.

Then both the uncoupling agent and the FAOI are discontinued for the next 5 to 7 days. During this rest period the Dnr protein level is raised and the essential fatty acid component restored.

After the aforesaid rest period the same treatment regimen is repeated, and so on until clinically complete tumor lysis is achieved. A subsequent recurrence would initiate a new series of treatment periods.

It should be noted that in the case where a patient remains in bed during the treatment period, the daytime $A_T$ becomes essentially equal to $B_T$, whence the overall therapeutic metabolic rate becomes equal to $B_T$ per se. Since $A_T$ is generally greater than $B_T$, the overall therapeutic metabolic rate and hence daily calorie intake rate can be reduced, while still maintaining the same uncoupling rate, by prescribing bed rest during the treatment periods.

EXAMPLE 3

The FAOI is administered in conjunction with the modified Dnr but without any uncoupling agent. The clinical regimen as described above is the same in all respects, e.g., the metabolic rate ($B_T$ and $A_T$) and respiratory quotient (RQ) measurements are made as usual, except that the uncoupling agent is not administered.

The dosage level of FAOI is the maximum tolerable or that which produces a significant rate of oncolysis, e.g. 5% to 10% reduction in tumor mass per day). It is contemplated that significant oncolysis rates can be achieved with FAOI alone at FAOI dosage levels producing a fatty acid oxidation rate inhibition of approximately 40 to 70 percent, provided that a very substantial increase in amino acid mobilization and oxidation rate and in the rate of glycolysis in the cancer cells does not occur. (See Example 8 hereinafter) The patient must be closely monitored for any indications of significant hypoglycemia development, as a safety precaution, when imposing high levels of fatty acid oxidation rate inhibition.

EXAMPLE 4

The following analytical model demonstrates the powerful effectuation of oncolysis by the preferred CUACTS plus FAOI embodiment of the present invention in cases where the CUACTS regimen alone is only marginally effective because of elevated endogenous fatty acid availability. Reference is made to FIG. 1.

$A\dot{T}P_{A,i}$ represents the actual in vivo ATP energy production rate of the tumor cells initially, before the administration of the Dnr, uncoupling agent, and FAOI of the present invention. One of the therapeutic protocols is to first administer the Dnr and uncoupling agent, followed by the FAOI. As the Dnr and uncoupling agent are initially administered the actual (net) ATP energy production rate of the tumor cells $A\dot{T}P_A$ remains constant and equal to $A\dot{T}P_{A,i}$, the energy wasting by the uncoupling being supplied by the increased rate of overall oxidation $ATP_P$ by the Respiratory Chain of the mitochondria. As the dosage of uncoupling agent is successively increased, the potential ATP energy production rate of the tumor cells ($A\dot{T}P_P$)(equal to the sum of the actual ATP production rate $A\dot{T}P_A$ and the equivalent of the ATP production rate that is being uncoupled, $\dot{U}$) first increases to a maximum level, $A\dot{T}P_{P_{max}}$, as limited by the availability of fatty acids and amino acids for oxidation. The aforesaid maximum level, termed $ATP_{P\,max}$, represents the maximum potential ATP energy production rate of the cancer cells at the prescribed therapeutic basal metabolic rate $B_T$ of approximately two times the standard basal metabolic rate $B_S$, before satiation limits the rate of intake of the Dnr. Given these parameters, the $ATP_{P\,max}$ rate is then set by the limiting availability of fatty acids at their normal plasma concentration.

Following the attainment of this $A\dot{T}P_{P\,max}$, the actual ATP energy production rate in the cancer cells $A\dot{T}P_A$ plummets as the dosage of uncoupling agent is further increased. As the uncoupling action then erodes the actual ATP production rate, the $A\dot{T}P_A$ decreases commensurately below the pretreatment $A\dot{T}P_{A,i}$ level. The extent of uncoupling ($\dot{U}$), is set by the therapeutically prescribed basal metabolic rate $B_T$. Ultimately, at an uncoupling rate $\dot{U}$ equivalent to a therapeutically prescribed basal metabolic rate corresponding to $B_T'=2.0$ (i.e., 2 times the standard basal metabolic rate $B_S$ of the patient), the $A\dot{T}P_A$ will have been depressed to a level about halfway between $A\dot{T}P_{A,i}$ and $A\dot{T}P_L$, $A\dot{T}P_L$ being the ATP energy production rate at which significant oncolysis (e.g. 20% to 30% decrease in tumor mass per day) results.

The foregoing situation, based on clinical observations of terminal cancer patients undergoing treatment with CUACTS (Dnr plus uncoupling agent, but without any FAOI), is representative of particular patients in which the existing fatty acid availability level in the plasma was high enough to prevent significant oncolysis at $B_T' = 2.0$. However, the malignant lesions of these patients became static (i.e. no further increase in tumor mass) when so treated at $B_T' = 2.0$. This condition indicates that the $\dot{ATP}_A$ in these patients was substantially depressed below $\dot{ATP}_{A,i}$, enough to stop cellular proliferation, but not down to the lethal level $\dot{ATP}_L$ necessary for very significant oncolysis to occur.

Thus, at $B_T' = 2.0$ (i.e., just before the Dnr intake satiation point is reached, conditions in the cancer cells are on the threshold of those required for effecting very significant oncolysis, from administration of the uncoupling agent and Dnr alone. The fatty acid concentration in the plasma is just enough (at its normal, i.e., pretreatment, level) to allow an $\dot{ATP}_{P\,max}$ which, at the satiation-limited therapeutic basal metabolic rate corresponding to $B_T' = 2.0$, prevents the associated $\dot{U}$ at $B_T' = 2.0$ from lowering $\dot{ATP}_A$ to the lethal level $\dot{ATP}_L$.

When an FAOI is now added in increasing dosage, while the Dnr and uncoupling agent are maintained to produce a therapeutic basal metabolic rate equivalent to $B_T' = 2.0$, the cancer cell fatty acid oxidation rate is reduced, and consequently the $\dot{ATP}_{Pmax}$ decreases. When the $\dot{ATP}_{Pmax}$ has been decreased to the level indicated by the dotted line in FIG. 1, the $\dot{U}$ (at $B_T' = 2.0$) will then be great enough to depress the $\dot{ATP}_A$ to the $\dot{ATP}_L$ level and very significant oncolysis will then occur. If the dosage of FAOI is further increased, the $\dot{ATP}_A$ is depressed below $\dot{ATP}_L$, corresponding to a massive rate of oncolysis (e.g., more than 20% decrease in tumor mass per day).

EXAMPLE 5

Reference is made to Example 4 and FIG. 1. The following data are based on actual human physical parameters and clinical tumor-response observations of a 70 kg cancer patient undergoing CUACTS therapy. This particular patient represents, as in Example 4, a case wherein the depression of $\dot{ATP}_A$ was not quite adequate at the therapeutic basal metabolic rate ($B_T' = 2.0$) to effect oncolysis (due to elevated plasma fatty acid availability), although full arrest of tumor growth was achieved.

| | | | |
|---|---|---|---|
| $\dot{ATP}_{Pmax}$ | = 30.60 | $\phi$ = | $\frac{\text{Kcal/day}}{\text{Kg cc}}$ |
| $\dot{ATP}_{A,i}$ | = 22.20 | cc = cancer cells | |
| $\dot{ATP}_L$ | = 17.80 | | |
| $\dot{U}$ ($B_T' = 2.0$) | = 9.50 | | |

The $\dot{ATP}_L$ rate is projected to lie about 20% below $\dot{ATP}_{A,i}$, the pretreatment actual ATP production rate of the tumor cells, or at a level of 17.8$\phi$. So, without FAOI the depression in the actual ATP energy production rate $\dot{ATP}_A = \dot{ATP}_{Pmax} - \dot{U}$ caused by the uncoupling agent falls 3.3$\phi$ short of reaching $\dot{ATP}_L$, in this particular patient. Therefore, to permit a depression of $\dot{ATP}_A$ to $\dot{ATP}_L$, the FAOI must be administered at dosage sufficient to depress $\dot{ATP}_{Pmax}$ by 3.3$\phi$ or a 10.8% depression of $\dot{ATP}_{P\,max}$. This is a relatively small depression indeed to achieve very significant oncolysis, especially when one considers that there are known FAOI such as, e.g., palmoxirate and hydrazine monohydrate which are capable of depressing fatty acid oxidation rates by 75% or more.

EXAMPLE 6

It is understood that the percentage of fatty acid oxidation inhibition per se required to depress the $\dot{ATP}_{P\,max}$ in Example 5 such that the existing $\dot{U}$ (=9.5 $\phi$) will force $\dot{ATP}_A$ to reach $\dot{ATP}_L$ in the cancer cells which may be much larger then 10.8%. This is because—although fatty acid oxidation is generally the predominant energy source in cancer cells, amino acid oxidation and/or glycolysis may contribute appreciably to the overall $\dot{ATP}_{P\,max}$, especially when the fatty acid oxidation rate is restricted. If $\dot{ATP}_{P\,max}$ is viewed as the composite value of the maximum potential rate derived from the additive contributions of the oxidation of fatty acids, amino acids and/or glycolysis of glucose, then the requisite depression of the potential ATP energy production rate $\dot{ATP}_{P\,max}$ caused by the FAOI in the cancer cells will reflect a relatively larger percentage of fatty acid oxidation inhibition per se vis-a-vis the percentage of overall depression of $\dot{ATP}_{P\,max}$. For example, if fatty acid oxidation were to constitute only 50% of the $\dot{ATP}_{P\,max}$ in Example 5, then the 10.8% depression of $\dot{ATP}_{P\,max}$ calculated thereabove would require a 21.6% inhibition of fatty acid oxidation per se. Even in such an extreme case—where fatty acid oxidation contributed only 50% of $\dot{ATP}_{P\,max}$—note that still only a relatively low rate of fatty acid oxidation inhibition is necessary, once the uncoupling agent has already provided some 31% $\dot{ATP}_{P\,max}$ wastage, to achieve very substantial oncolysis. Thus, in this case the uncoupling provides 74.2% and the fatty acid oxidation inhibition 25.8% of the required reduction from $\dot{ATP}_{P\,max}$ to $\dot{ATP}_L$.

It must be emphasized that there is an inverse relationship between the quantities of uncoupling agent and FAOI required to depress the $\dot{ATP}_A$ in tumor cells sufficiently to achieve very significant oncolysis. Calculations made in conformance with the above-described model show that as the therapeutic basal metabolic rate is reduced from the level corresponding to $B_T' = 2.5$ (i.e., 2.5 times the standard basal metabolic rate ($B_S$) of the patient) for down to $B_T' = 1.0$, the amount of concurrently administered FAOI required to achieve very significant oncolysis increases from 0 to that dosage required to produce a 40.0 percent reduction in $\dot{ATP}_{P\,max}$. And, of course, said 40.0 percent inhibition of $\dot{ATP}_{P\,max}$ corresponds to a therapeutic regimen wherein a FAOI is administered without any uncoupling agent, i.e., $\dot{U} = 0$. As discussed hereinabove, this 40% reduction in $\dot{ATP}_{P\,max}$ corresponds to a 66% inhibition of the fatty acid oxidation rate in the case where the fatty acid oxidation rate comprises 60% of the $\dot{ATP}_{P\,max}$ of the cancer cells initially.

Thus at any elevated therapeutic basal metabolic rate achieved by the uncoupling agent corresponding to between $B_T' = 2.5$ (substantially the maximum clinically tolerable level for extended periods) and $B_T' = 1.0$, there is a corresponding percentage of fatty acid oxidation rate inhibition which is necessary to achieve very significant oncolysis. The same rate of oncolytic action can be achieved with any of these combinations. Nevertheless, it is preferable to simultaneously use the maximum possible—commensurate with the avoidance of tumor-product toxemia—degrees of fatty acid oxidation inhibition and oxidative phosphorylation uncoupling so as to absolutely maximize the rate and extent of oncolysis. As noted above, the maximum clinically feasible metabolic rate is set by the advent of Dnr intake satiation. Thus a therapeutic basal metabolic rate $B_T$ corresponding to $B_{T'}=2.5$ is approximately the maximum metabolic rate clinically usable in the present CUACTS+FAOI therapy with the modified Dnr regimen embodiment specifically described herein. At higher therapeutic basal metabolic rates the patient cannot take glucose into the body at an adequate rate, even with maximal parenteral supplementation to balance the caloric expenditure rate, and thus severe hypoglycemia could develop in a short time above a therapeutic basal metabolic rate corresponding to $B_{T'}=2.5$, at maximal (50%-60%) tolerable rates of fatty acid oxidation inhibition.

Although $B_{T'}$ levels as high as 3.5 are physiologically tolerable in constitutionally uncompromised patients and are readily attainable with adequate dosage levels of the uncoupling agent, the extensive and rapid mobilization of endogenous fatty acids to compensate for the caloric intake deficiency (due to Dnr satiation) which occurs above $B_{T'}=2.5$ grossly increases the fatty acid availability for oxidation. This increase raises the $ATP_P$ $_{max}$ level several times more than the concomitant increase in U̇. Calculations similar to those in Example 5 indicate that at $B_{T'}=3.5$ with the CUACTS+FAOI regimen, more than 75% inhibition of the fatty acid oxidation rate would be required in addition to the $B_{T'}=3.5$ uncoupling rate (U̇), per se to achieve very significant oncolysis. Moreover, at such elevated $B_{T'}$ levels, which appreciably exceed the $B_{T'}$ level at which satiation occurs, the consequent caloric deficiency soon exhausts the glycogen stores of both liver and muscle and leads to severe, ultimately lethal, hypoglycemia if maintained for more than a short while.

EXAMPLE 7

The following example demonstrates the dramatic rate and extent of oncolysis that are achievable in human cancer patients with otherwise totally refractory malignant neoplasms by use of the present CUACTS+FAOI invention.

A 45-year old female patient with far-advanced infiltrating ductal cell carcinoma of the breast was treated with the basic CUACTS regimen. This patient had been judged terminal following rapid progression of her disease over the entire left chest wall, despite initial radical mastectomy and extensive radiotherapy, and subsequent intensive combination chemotherapy with multiple mitotoxic agents. During the CUACTS treatment at elevated $B_T$, the patient was found to possess a substantial deficiency in ability to oxidize fatty acids at an appreciable rate, demonstrating the classical clinical symptoms of Fatty Acid Oxidation Deficiency Syndrome associated with a genetic deficiency of the enzyme Carnitine Palmitoyl Transferase required for transport of fatty acids into cellular mitochondria (see, e.g., Cumming, W. J. K. et al, Journal of the Neurological Sciences 30:247-258. 1976). This patient, therefore, had a naturally endowed FAOI which, in combination with the CUACT SYSTEM, constituted precisely the CUACTS F regimen of the present invention, but with the Dnr regimen constituting the preferred embodiment of the CUACTS per se (i.e., six daytime nutritional cocktails). This patient experienced a dramatically rapid and complete (100%) regression of her clinically detectable tumors, after only three 24-hour treatment periods at elevated $B_T$. This response was much more extensive than is generally seen in the same time period with the CUACTS alone, in patients with the same type of cancer, demonstrating the significant enhancement of efficacy engendered by the concomitant use of FAOI with the basic CUACTS. This dramatic rate and extent of oncolysis obtained despite the fact that the patient was some 17 pounds overweight at the time of treatment and was on the six-cocktail Dnr, testifying to the importance of fatty acid availability as the major source of cancer cell ATP energy production, as well as the power of the FAOI in blocking this availability most effectively to yield very significant oncolysis in combination with the Cuacts.

EXAMPLE 8

In regard to the special case of the present invention wherein the FAOI alone is utilized without the uncoupling agent, the following example is illustrative. Reference is made to FIG. 1.

In the case where FAOI alone is used, there is no elevation in the therapeutic basal metabolic rate $B_T$, which remains equal to the pretreatment basal metabolic rate throughout the treatment period, since there is no uncoupling wastage of energy. The cancer cell $\dot{ATP}_{A,i}$ level (i.e., pretreatment) is 22.2$\phi$ of which the fatty acid oxidation rate is assumed to contribute approximately 70% and the amino acid oxidation+glycolysis rates 30%, i.e., 70% (in this particular example) of the pretreatment energy production per unit time of the cancer cells is derived from the oxidation of fatty acids. When the FAOI is first administered, the fatty acid oxidation rate is decreased, but the amino acid oxidation and glycolysis rates increase in homeostatic response to compensate for the decrease in the fatty acid oxidation rate, with the net result that the $\dot{ATP}_A$ level remains constant and equal to $\dot{ATP}_{A,i}$. Eventually, however, as the dosage of FAOI is successively increased, the increasing amino acid oxidation plus glycolysis rates reach a maximum, whence any further increase in the FAOI dosage level causes the associated decrease in fatty acid oxidation rate to effect a net decrease in $\dot{ATP}_A$, depressing it below $\dot{ATP}_{A,i}$. Ultimately, with increasing FAOI dosage (i.e., increasing percentage inhibition of the fatty acid oxidation rate of the cancer cell), $ATP_A$ is depressed to the lethal $\dot{ATP}_L$ level and very significant oncolysis ensues.

In the case of FAOI alone, there is no actual increase in the rate of oxidation by the Respiratory Chain of the mitochondria, and no increase in the total fatty acid oxidation rate of the cancer cell as occurs in the case of uncoupling agent use. Consequently, the equivalent "$\dot{ATP}_{Pmax}$" is considerably less than in the case of O-P uncoupling, the equivalent FAOI-alone "$\dot{ATP}_{Pmax}$" being equal to $\dot{ATP}_{A,i}$ plus only the increase in the amino acid oxidation+glycolysis ATP production rates. Thus, with reference to FIG. 1, if the increase in fatty acid oxidation rate due to the uncoupling is assumed to provide nominally 60% of the $\dot{ATP}_{Pmax}$-$-\dot{ATP}_{A,i}$ increase in potential energy production rate, with the increased amino acid oxidation+glycolysis ATP production rates accounting for the remainder (which is equal to the maximum increase in the amino acid oxidation+glycolysis rates with the FAOI alone), then the equivalent "$\dot{ATP}_{Pmax}$" of the cancer cells with FAOI alone is 25.6$\phi$. (Note that in the case of FAOI alone the equivalent "$ATP_{Pmax}$" elevation above $\dot{ATP}_{A,i}$ represents the decrease in fatty acid oxidation rate which is compensated for by the homeostatic increase in the amino acid oxidation+glycolysis ATP production rates prior to any decrease in $\text{A\dot{T}P}_A$, and is not an actual energy wastage as in the case of uncoupling per se). With the fatty acid oxidation rate contributing 70% of $\text{A\dot{T}P}_{A,i}$ (or 11.1$\phi$), as stated above, the overall percentage inhibition of fatty acid oxidation rate required to depress the equivalent "$\text{A\dot{T}P}_{Pmax}$" to $\text{A\dot{T}P}_L$ is 50.2% (7.8$\phi$ units). If instead of the fatty acid oxidation rate contributing 70% of $\text{ATP}_{A,i}$, the contribution was only 50% (with the amino acid oxidation+glycolysis ATP production rates contributing the other 50%), the overall percentage inhibition of fatty acid oxidation rate would have to be 70.3%. Ultimately, if the fatty acid oxidation rate contributed only 35% or less of the $\text{A\dot{T}P}_{A,i}$, even with 100% inhibition of the fatty acid oxidation rate, very significant oncolysis could not be achieved by the FAOI alone (i.e., the increased amino acid oxidation+glycolysis ATP production rates would be adequate to provide the minimal survival ATP production rate of the cancer cells). Thus, in cases where the fatty acid oxidation rate contributes at least 50% of the $\text{A\dot{T}P}_{A,i}$ of the cancer cell, very significant oncolysis is achievable with FAOI alone, albeit at high, but generally clinically tolerable, levels of fatty acid oxidation rate inhibition.

It should be emphasized here that the contributions of the uncoupling agent and the FAOI in the CUACTS F regimen are independent and directly additive with respect to lowering the $\text{A\dot{T}P}_A$ to $\text{A\dot{T}P}_L$ to effect very significant oncolysis. Consequently, the power of the combined CUACTS+FAOI regimen to effect very significant oncolysis generally in a diversity of malignant neoplasm types, considering that the uncoupling aspect alone and the fatty acid oxidation alone are each individually capable of effecting significant oncolysis, is manifest.

It must be emphasized that if a maximum percentage of fatty acid oxidation inhibition is employed it is essential that overall daily caloric balance be maintained at all times, that is, the maximum elevated overall therapeutic metabolic rate achieved with the uncoupling agent (i.e., $\frac{1}{2}(B_T+A_T)$) must not exceed that which can be calorically satisfied by the combined Dnr dietary and parenterally supplied caloric intake. And each individual patient must be carefully monitored to discern his or her satiation limit, beyond which exogenously-supplied glucose cannot be assimilated. Otherwise severe and potentially lethal hypoglycemia could develop, since the capacity to mobilize and utilize endogenous fatty acids for normal cell energy production—the body's usual homeostatic safety defense in such cases—will be greatly impaired by the concomitant administration of FAOI at high dosage.

Consequently, the preferred clinical regimen for use in this invention comprises imposition of the maximum tolerable percentage of fatty acid oxidation inhibition (approximately 50%) and the maximum level of uncoupling commensurate with but not exceeding the Dnr intake satiation level ($B_T'$ equal to approximately 2.0, but possibly as high as 2.5 with the herein described modified Dnr regimen). This protocol will yield, according to the Example 6, a depression of the net cancer cell ATP production rate $\text{A\dot{T}P}_A$ which is considerably in excess of that needed to produce a significant oncolytic rate. Imposition of said excess is consistent with the general oncologic principle that with cancer one should always utilize the fullest antineoplastic force available, commensurate with a preclusion of the potential problem of tumor-product toxemia, in the case of a very large tumor burden. It is noteworthy that the potential problem of tumor-product toxemia has never materialized during administration of CUACTS per se, even in cases of massive and rapid oncolysis. Presumptively, the tumor cells may be significantly reduced in mass by autophagy in response to the high oxidative rates imposed, prior to cell death, as well as being rapidly scavenged by antigenically stimulated macrophage populations (populations which are destroyed during blastogenesis by conventional mitotoxin chemotherapy, but which remain unharmed in CUACTS and the present modified CUACTS).

What is claimed is:

1. In a method of treating a mammal having a malignant neoplasm wherein the cells of said malignant neoplasm are substantially unable to utilize glucose for the production of adenosine triphosphate (ATP) by elevating said mammal's basal metabolic rate as far as therapeutically tolerable by administering a combination of
    (a) a predetermined periodic dosage of a physiologically tolerable uncoupling agent and
    (b) a daily nutritional regimen selected with reference to said mammal's basal and active metabolic rates so as to provide only said mammal's minimum daily caloric requirement, allocated among the minimum amount of amino acids to maintain minimal bodily nitrogen balance, a minimum amount of essential fatty acids and glucose or physiological precursors thereof, the improvement which comprises also administering a predetermined periodic dosage of fatty acid oxidation inhibitor sufficient to minimize the mitochondrial $\beta$-oxidation rate within physiologically tolerable limits.

2. The method of claim 1 wherein said minimum amount of essential fatty acids in said daily nutritional regimen is zero during at least a part of the treatment.

3. The method of claim 1 in which said periodic dosage of said uncoupling agent and said daily nutritional regimen are reevaluated and adjusted in accordance with measured changes in said mammal's basal and active metabolic rates.

4. The method of claim 1 wherein said uncoupling agent is selected from among 2,4-dinitrophenol, 2,6-dinitrophenol, 4,6-dinitrocresol, and mixtures of any of them.

5. The method of claim 1 wherein said periodic dosage of uncoupling agent, during at least a part of the treatment, is zero.

6. The method of claim 1 wherein said fatty acid oxidation inhibitor is selected from among methyl 2-tetradecylglycidate, 2-tetradecylgylcidic acid, and mixtures thereof.

7. A method according to any of the preceding claims wherein any or all of the minimum daily caloric requirement, uncoupling agent, and fatty acid oxidation inhibitor may be administered orally or parenterally.

8. A method according to claim 7 wherein the minimum daily caloric requirement, expressed as kilocalories, per day, is measured at about one-half the sum of said mammal's basal and active metabolic rates, each expressed in kilocalories per day.

9. A method according to claim 7 wherein said amount of amino acids provides daily nitrogen intake for said mammal substantially equal to the minimum total daily nitrogen excreted in urine by said mammal and said minimum amount of fatty acids corresponds to about 1% of said minimum daily caloric requirement at the commencement of administration of the method as described in claim 1.

10. A method according to claim 7 wherein said mammal is a human being.

11. A method according to any of claims 1-6 wherein the minimum daily caloric requirements, expressed as kilocalories per day, is measured at about one-half the sum of said mammal's basal and active metabolic rates, each expressed in kilocalories per day.

12. A method according to claim 11 wherein said amount of amino acids provides daily niotrogen intake for said mammal substantially equal to the minimum total daily nitrogen excreted in urine by said mammal and said minimum amount of fatty acids corresponds to about 1% of said minimum daily caloric requirement at the commencement of administration of the method as described in claim 1.

13. A method according to claim 11 wherein said mammal is a human being.

14. A method according to any of claims 1-6 wherein said amount of amino acids provides daily nitrogen intake for said mammal substantially equal to the minimum total daily nitrogen excreted in urine by said mammal and said minimum amount of fatty acids corresponds to about 1% of said minimum daily caloric requirement at the commencement of administration of the method described in claim 1.

15. A method according to claim 14 wherein said mammal is a human being.

16. A method according to any of claims 1-6 wherein said mammal is a human being.

17. A method according to claim 16 wherein said human being's basal metabolic rate is elevated to a level between about 1.5 and 2.5 times the Mayo Normal Standard basal metabolic rate for said human being.

18. A method according to claim 16 wherein the therapeutic basal metabolic rate is maintained at a level wherein overall caloric balance is equal to the satiation limit of the individual patient.

19. A method according to claim 16 wherein the percentage inhibition of the fatty acid oxidation rate is between about 20% and about 60% as determined by respiratory quotient measurements.

20. A method according to claim 16 wherein said daily nutritional regimen supplies protein at a level between about 0 grams and about 20 grams of protein per day per 70 grams of body weight of said human being, said human being's basal metabolic rate is elevated to a level between about 1.8 and 2.0 times the Mayo Normal Standard basal metabolic rate for said human being, and the percentage of inhibition of the fatty acid oxidation rate is maintained for prescribed periods between about 20% and about 60%.

21. In a method for selectivity decreasing the rate of ATP production in those malignant cells of a mammal which substantially lack the capability to utilize glucose to produce ATP without substantially altering the rate of ATP production in normal cells of said mammal in which said mammal's basal metabolic rate is elevated as far as therapeutically tolerable by administering a combination of (a) a predetermined periodic dosage of a physiologically tolerable uncoupling agent and
(b) a daily nutritional regimen selected with reference to said mammal's basal and active metabolic rates so as to provide only said mammal's minimum daily caloric requirement, allocated among the minimum amount of amino acids to maintain minimal bodily nitrogen balance, a minimum amount of essential fatty acids and glucose or physiological precursors thereof, the improvement which comprises also administering a predetermined periodic dosage of fatty acid oxidation inhibitor sufficient to minimize the mitochondrial $\beta$-oxidation rate within physiologically tolerable limits.

* * * * *

UNITED STATES PATENT AND TRADEMARK OFFICE
CERTIFICATE OF CORRECTION

PATENT NO. : 4,724,230

DATED : February 9, 1988

INVENTOR(S) : Clarence D. Cone, Jr.

It is certified that error appears in the above-identified patent and that said Letters Patent is hereby corrected as shown below:

Col 7, line 65, delete "of" from the phrase "glucose of" and add "to" in its place so that the line reads "glucose to"

Col 10, line 5, add "(" before "e.g. 5%" so that it reads "(e.g. 5%"

Col 11, line 15, add ")" after "reached," so that it reads "reached),"

Col 14, line 13, make "Cuacts" reads "CUACTS"

Signed and Sealed this

Fifteenth Day of November, 1988

Attest:

DONALD J. QUIGG

*Attesting Officer*   *Commissioner of Patents and Trademarks*